(12) United States Patent
Kawainshi et al.

(10) Patent No.: US 6,704,944 B2
(45) Date of Patent: Mar. 16, 2004

(54) SPORTS GOGGLES

(75) Inventors: Noboru Kawainshi, Higashiosaka (JP); Kimio Matsumoto, Matsubara (JP); Toru Tsubooka, Sakurai (JP)

(73) Assignee: Yamamoto Kogaku Co., Ltd., Osaka (JP)

( * ) Notice: Subject to any disclaimer, the term of this patent is extended or adjusted under 35 U.S.C. 154(b) by 116 days.

(21) Appl. No.: 10/138,123

(22) Filed: May 3, 2002

(65) Prior Publication Data

US 2002/0166159 A1 Nov. 14, 2002

(30) Foreign Application Priority Data

May 8, 2001 (JP) .................................... 2001-137699

(51) Int. Cl.⁷ ................................................ A61F 9/02
(52) U.S. Cl. ........................................ 2/436; 2/171.3
(58) Field of Search ........................ 2/436, 437, 171.3, 2/8, 9; 351/158

(56) References Cited

U.S. PATENT DOCUMENTS

| | | | | |
|---|---|---|---|---|
| 5,813,990 A | * | 9/1998 | Ryll | 351/158 X |
| 6,049,917 A | * | 4/2000 | Ryden | 2/436 |
| 6,409,338 B1 | * | 6/2002 | Jewell | 351/158 |

* cited by examiner

*Primary Examiner*—Peter Nerbun
(74) *Attorney, Agent, or Firm*—Koda & Androlia

(57) ABSTRACT

Sports goggles include a goggle frame, a goggle lens fitted in the goggle frame, a strap coupled to the goggle frame at coupling positions on the right and left sides of the goggle frame. The sports goggles also include a ventilation fan system having a ventilation fan. In the system, a ventilation fan unit is provided on an upper portion of the goggle frame, a power supply unit is provided on one of right and left end areas below the coupling positions, and a switch unit is provided on the other area. The sports goggles provide a wearer with comfortable fitting and easy manipulation of the switch for the ventilation fan system.

12 Claims, 13 Drawing Sheets

US 6,704,944 B2

SPORTS GOGGLES

BACKGROUND OF THE INVENTION

1. Field of the Invention

The present invention relates to sports goggles, more particularly sports goggles used in skiing or a motorcycle tour.

2. Prior Art

Conventional sports goggles of this type have been known as those with a ventilation fan system in order to prevent clouding of a goggle lens or an eyeglass lens for correcting the eyesight of a wearer of goggles.

The foregoing ventilation fan system includes a ventilation fan unit, a power supply unit and a switch unit. One example is shown in the Japanese Utility Model Publication No. 2-19787, which has all of these units in an upper peripheral wall area of the goggle frame. Another example is shown in the Japanese Utility Model Publication No. 63-23073, which has only the ventilation fan unit in the center area of the upper peripheral wall and the power supply unit and the switch unit are provided on one side of a headband (or a strap) near the goggle frame.

However, the above conventional sports goggles have drawbacks. For instance, the sports goggles in the Japanese Utility Model Publication No. 2-19787, in which all of the ventilation unit, the power supply unit and the switch unit are provided in the upper peripheral wall area, provide poor cushioning property and inferior comfort. Furthermore, the upper peripheral wall area does not have enough space for an opening and this results in less air-flow from the upper peripheral wall and causes poor ventilation efficiency. In addition, in this type of sports goggles, since the switch unit is provided in the upper peripheral wall area, when a wearer has the goggles on and manipulates the switch unit, he or she must raise his or her hand up to above his or her eyes and this manipulation is often not easy.

On the other hand, in the conventional sports goggles in the Japanese Utility Model Publication No. 63-23073, since the power supply unit and the switch unit are provided on one side of the strap near the goggle frame, this side becomes heavier than the other side. This deteriorates the weight balance when a wearer has the goggles on and provides uncomfortable fitting to the wearer.

It is therefore an object of the present invention to provide sports goggles in which the above drawbacks are eliminated. More particularly it is an object of the present invention to provide sport goggles which produces a high comfortability, a high ventilation efficiency, an easy manipulation of a ventilation fan system, and guarantees a well weight balance and a good fitting on a wearer.

SUMMARY OF THE INVENTION

In order to achieve the above object, sports goggles of the present invention includes a goggle frame, a goggle lens fitted in the goggle frame, and a strap coupled to the goggle frame at coupling positions on the right and left sides of the goggle frame. On an upper portion of the goggles frame is provided a ventilation fan unit for a ventilation fan system. One of lateral end areas below the coupling positions of the strap is provided with a power supply unit for the ventilation fan system, and the other area is provided with a switch unit therefor.

In the sports goggles of the present invention, the goggle frame includes openings respectively on the upper portion, and the lateral right and left end areas below the coupling positions of the strap. With keeping a ventilation state through these openings, the sport goggles have the ventilation fan unit, the supply power unit and the switch unit.

In the sport goggles of the present invention, the ventilation fan unit, the power supply unit, and the switch unit are detachably provided to these respective openings.

Further, in the sports goggles of the invention, the switch unit includes an operation switch and a misoperation preventive switch for the ventilation fan provided in the ventilation fan unit. The operation switch can be manipulated from outside of the goggle frame and the misoperation preventive switch can be manipulated from inside of the goggle frame.

Moreover, in the sports goggles of the present invention, a step is formed on the inside of the upper peripheral edge area of the goggle lens. Along with the step, electric wiring or printed wiring extending from the ventilation fan unit to the power supply unit and the switch unit is provided.

The above and other objects, features and advantages of the present invention will become apparent from the following description read in conjunction with the accompanying drawings, in which like reference numerals designate the same elements.

DETAILED DESCRIPTION OF THE INVENTION

Figure 1:
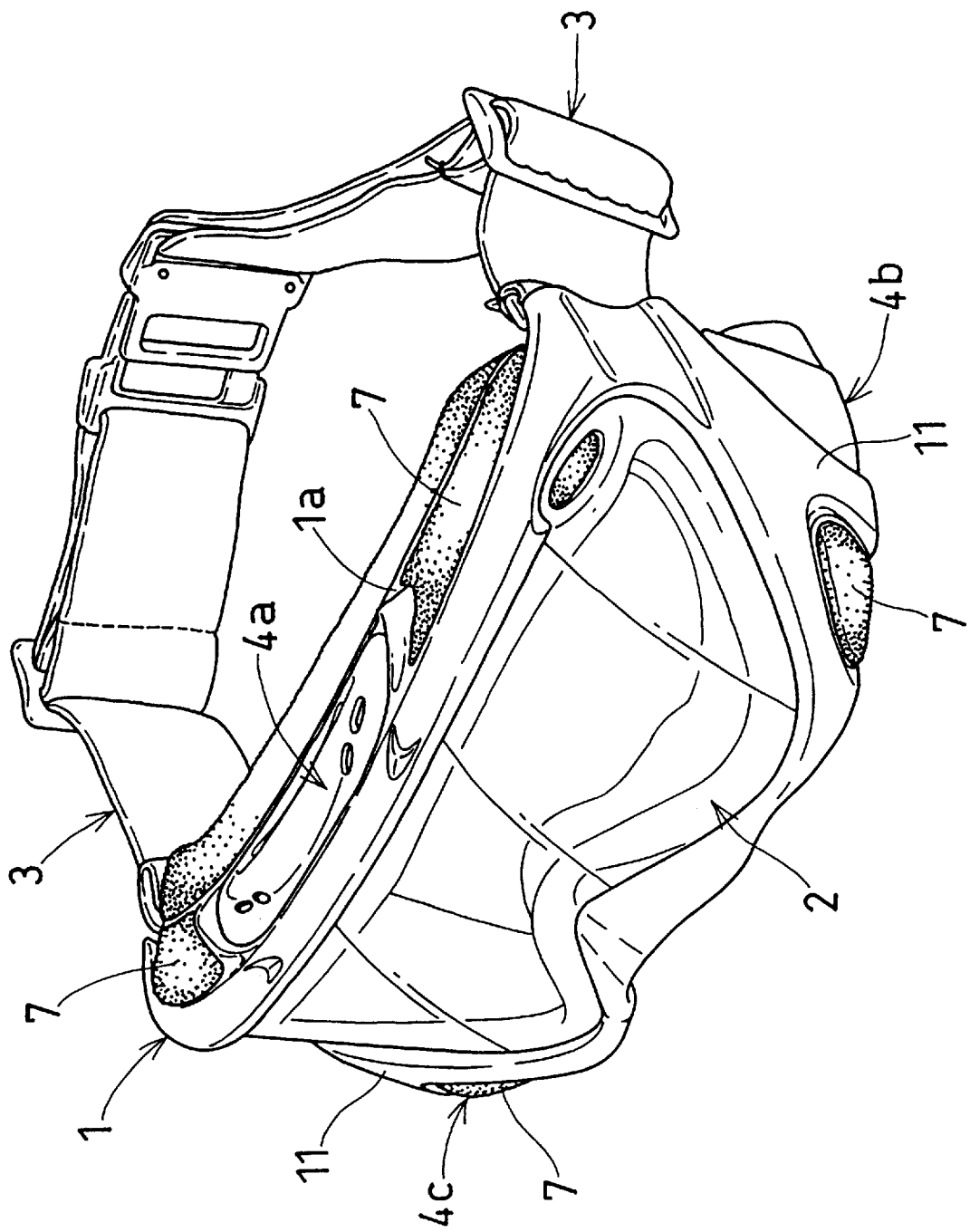
FIG. 1 is a perspective view showing an embodiment of sports goggles of the present invention.
Figure 2:
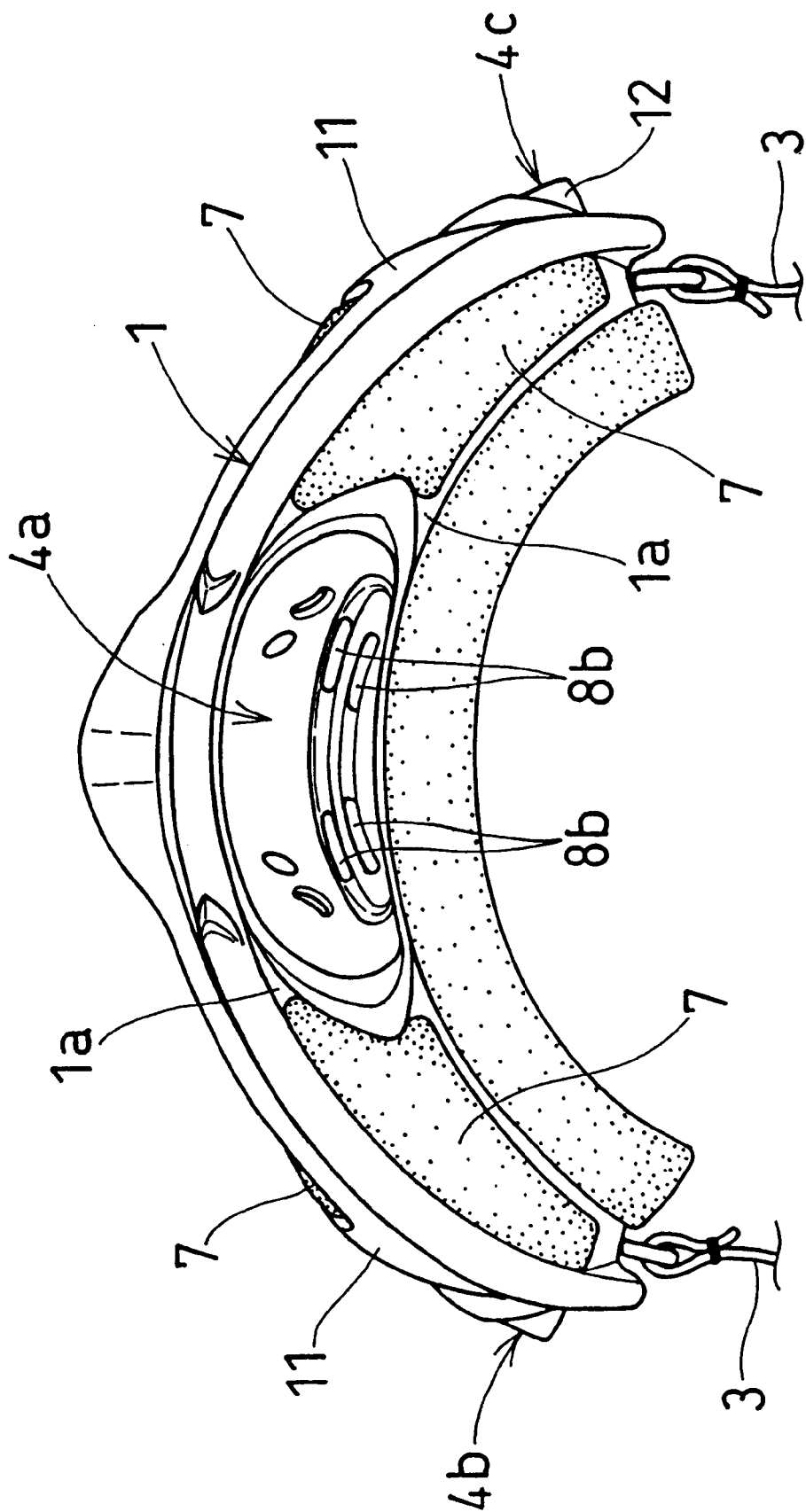
FIG. 2 is a plan viewing showing the sports goggles of the present invention in FIG. 1 in which a strap is omitted.
Figure 3:
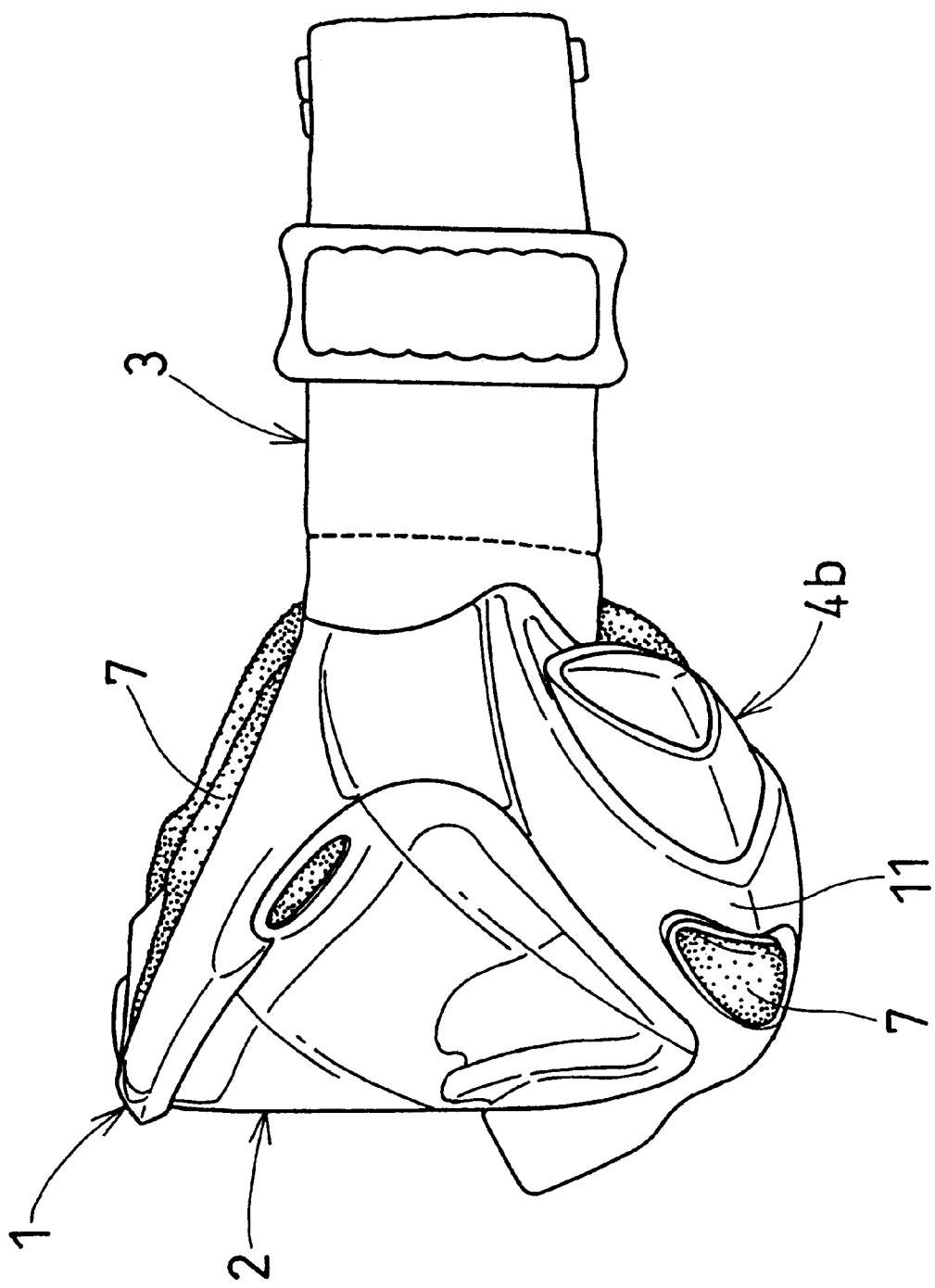
FIG. 3 is a side view of the sports goggles of the present invention in FIG. 1.
Figure 4:
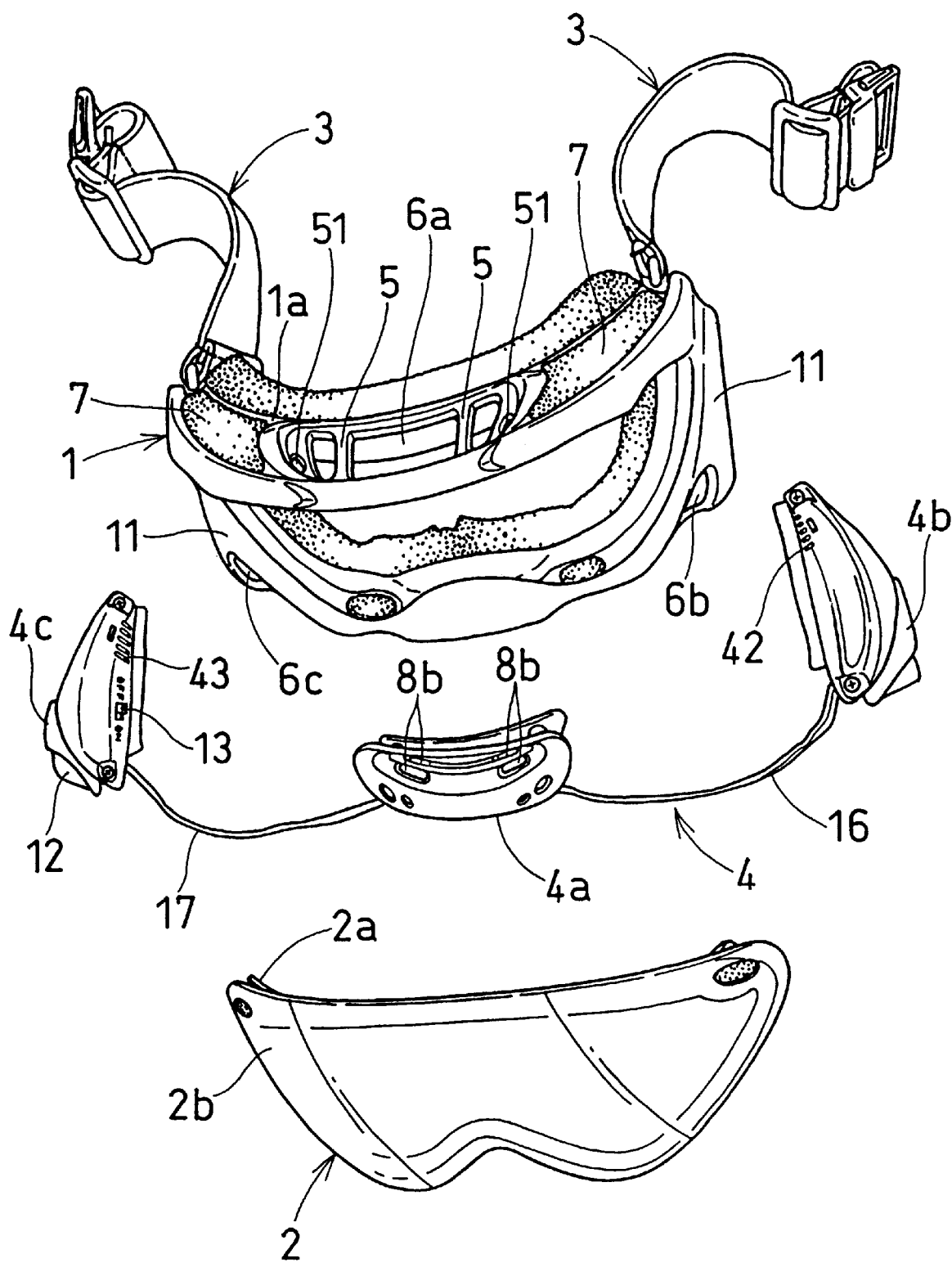
FIG. 4 is a perspective exploded view of the sports goggles of the present invention in FIG. 1.

Sports goggles of the present invention are illustrated in FIGS. 1 to 4. The sports goggles include a goggle frame 1, a goggle lens 2 fitted in the goggle frame 1, and a strap (or a headband) 3 coupled to a right and a left side of the goggle frame 1. On the upper part of the goggle frame 1 is provided a ventilation fan unit 4a of a ventilation fan system 4. The goggle frame 1 has a power supply unit 4b of the ventilation fan system 4 on one of the right and left end areas of the goggle frame 1 below coupling positions of the strap 3 and the right and left sides of the goggle frame 1, and at the other end area, a switch unit 4c of the ventilation fan system 4 is provided.

The goggle frame 1 is made of soft synthetic resin or the like. An upper peripheral wall member 1a provided in the upper part of the frame 1 has, in its center and both side portions, openings 6a, each of which is divided by a partition frame 5. To the opening 6a at the center, the ventilation fan unit 4a is detachably provided, while the openings 6 at the both sides are covered with permeable covers 7 such as made of polyurethane foam so as to maintain a ventilation state. The ventilation fan unit 4a is detachably provided to the center opening 6a in a fashion that the ventilation fan unit 4a is fitted with the partition frame 5, and an engaging claw 41 protruded from a ventilation fan unit body is engaged detachably with an engaging hole 51 formed on the partition frame 5. The cover 7 has a cushioning property, which provides comfortable fitting.

Figure 5:
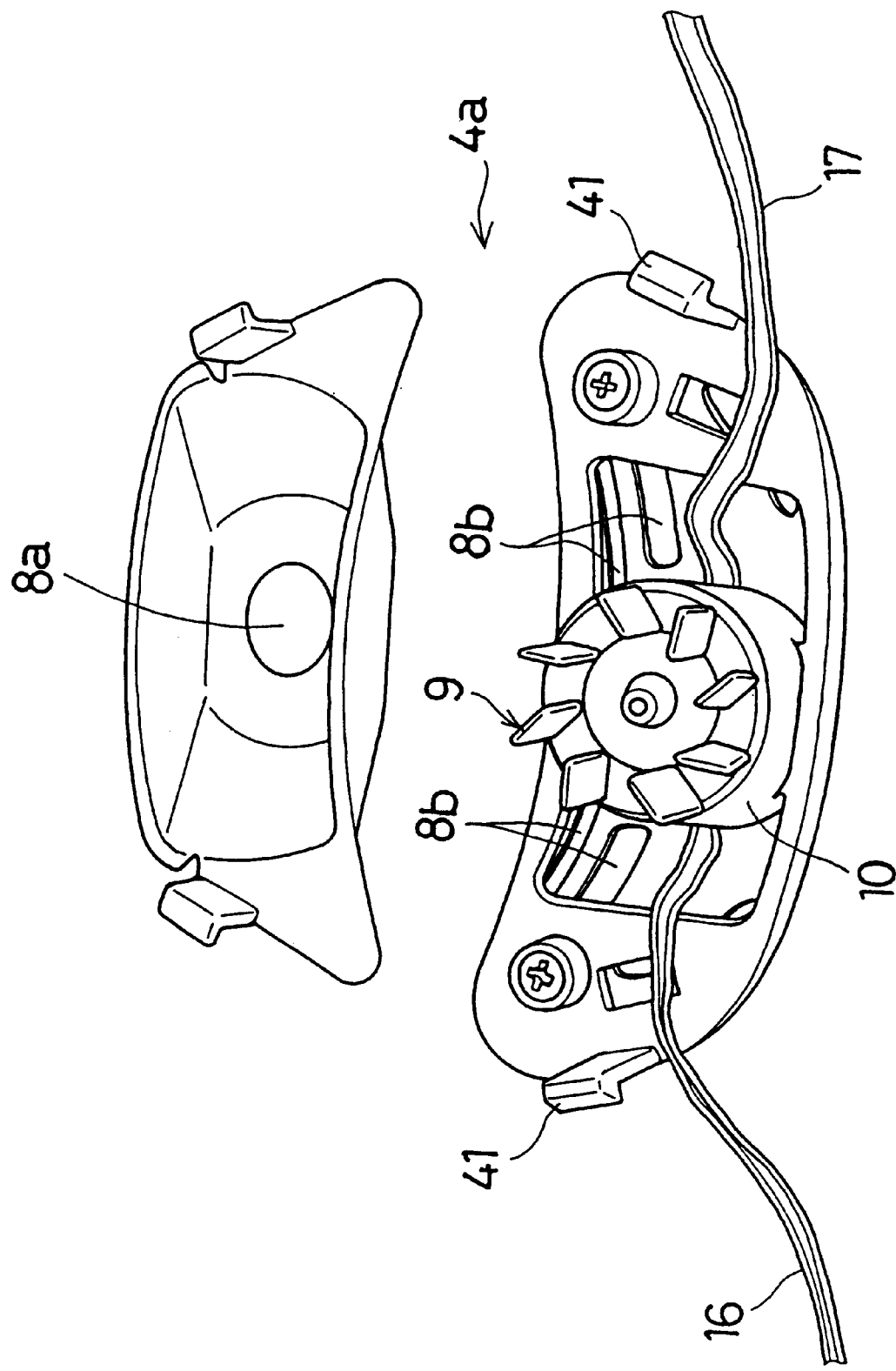
FIG. 5 is a perspective exploded view of a ventilation fan unit of the sports goggles of the present invention.

The ventilation fan unit 4a is clearly illustrated in FIG. 5, and has a unit body with an inhale port 8a and an exhale port 8b. Within the unit body, a ventilation fan 9 such as an axial flow fan is housed. The unit body is formed as a two-divided body. The inhale port 8a is formed in one, and the exhale port 8b is formed in the other. A motor 10 is fixed therewith, and a ventilation fan 9 is fitted to an output shaft of the motor 10.

The goggle frame 1 also has, on its front frame 11, openings 6b, 6c on both the lateral (right and left) end portions below the right and left coupling positions of the strap 3. The opening 6b is detachably provided with the power supply unit 4b and the opening 6c is detachably provided with the switch unit 4c. The power supply unit 4b and the switch unit 4c are detachably provided with the goggle frame in a way that they are detachably fitted into within the openings 6a, 6b of the front frame 11.

The power supply unit 4b houses a power source such as a dry cell therein. An opening (not shown) is formed on an outer side and covered with a permeable cover made of polyurethane foam or the like. Plural slit openings 42 are formed on an inner side. This construction enables to maintain a ventilation state of the opening 6b.

The switch unit 4c houses a switch mechanism therein. An opening (not shown) is formed on an outer side and covered with a permeable cover made of polyurethane foam or the like. Plural slit openings 43 are formed on an inner side. This construction enables to maintain a ventilation state of the opening 6c. The switch unit 4c has an operation switch 12 and a misoperation preventive switch 13 for the ventilation fan 9 provided in the ventilation fan unit 4a. The operation switch 12 can be manipulated from outside of the goggle frame 1, and the misoperation preventive switch 13 can be manipulated from inside of the goggle frame 1. The misoperation preventive switch 13 is to prevent misoperation of the operation switch 12, and unless the misoperation preventive switch 13 is kept in an OFF state, the ventilation fan 9 does not rotate even if the operation switch 12 is set in an ON state. Therefore, when the goggles are on, the misoperation preventive switch 13 is kept in an OFF state, and the ventilation fan may be driven or stopped by the manipulation of the operation switch 12. On the other hand, when the goggles are not on, the misoperation switch 13 is kept in an ON state, so that the ventilation fan 9 may not be driven even if the operation switch 12 is turned on.

Figure 6:
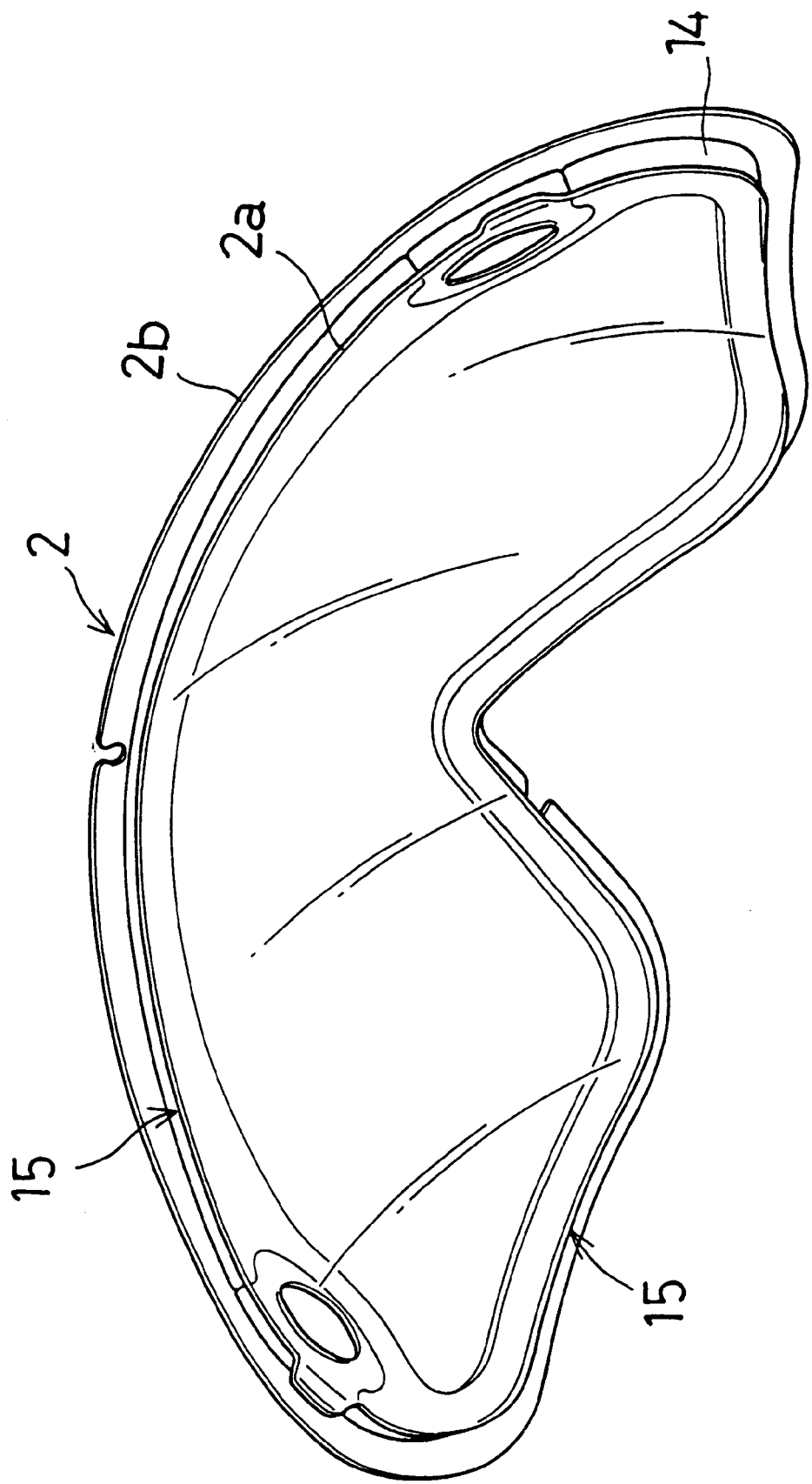
FIG. 6 is a perspective backside view of a goggle lens of the sports goggles of the present invention.

The goggle lens 2 is made of a lens plate of transparent synthetic resin or the like. As shown in FIG. 6, the goggles lens 2 includes an inner lens plate 2a and an outer lens plate 2b, the former is one size smaller than the latter. A flexible frame body 14 of chloroprene rubber or the like is adhered to the peripheral edge area of the inner lens plate 2a. The inner lens plate 2a and the outer lens plate 2b are joined together through the frame body 14, which gives a space therebetween.

Further, joining the inner lens plate 2a and the outer lens plate 2b together accordingly produces a step 15 inside of the peripheral edge area of the goggle lens 2. Without using two inner and outer lens plates, this step 15 may also be formed optionally on a goggle lens with a single lens plate by a bending process.

Figure 7:
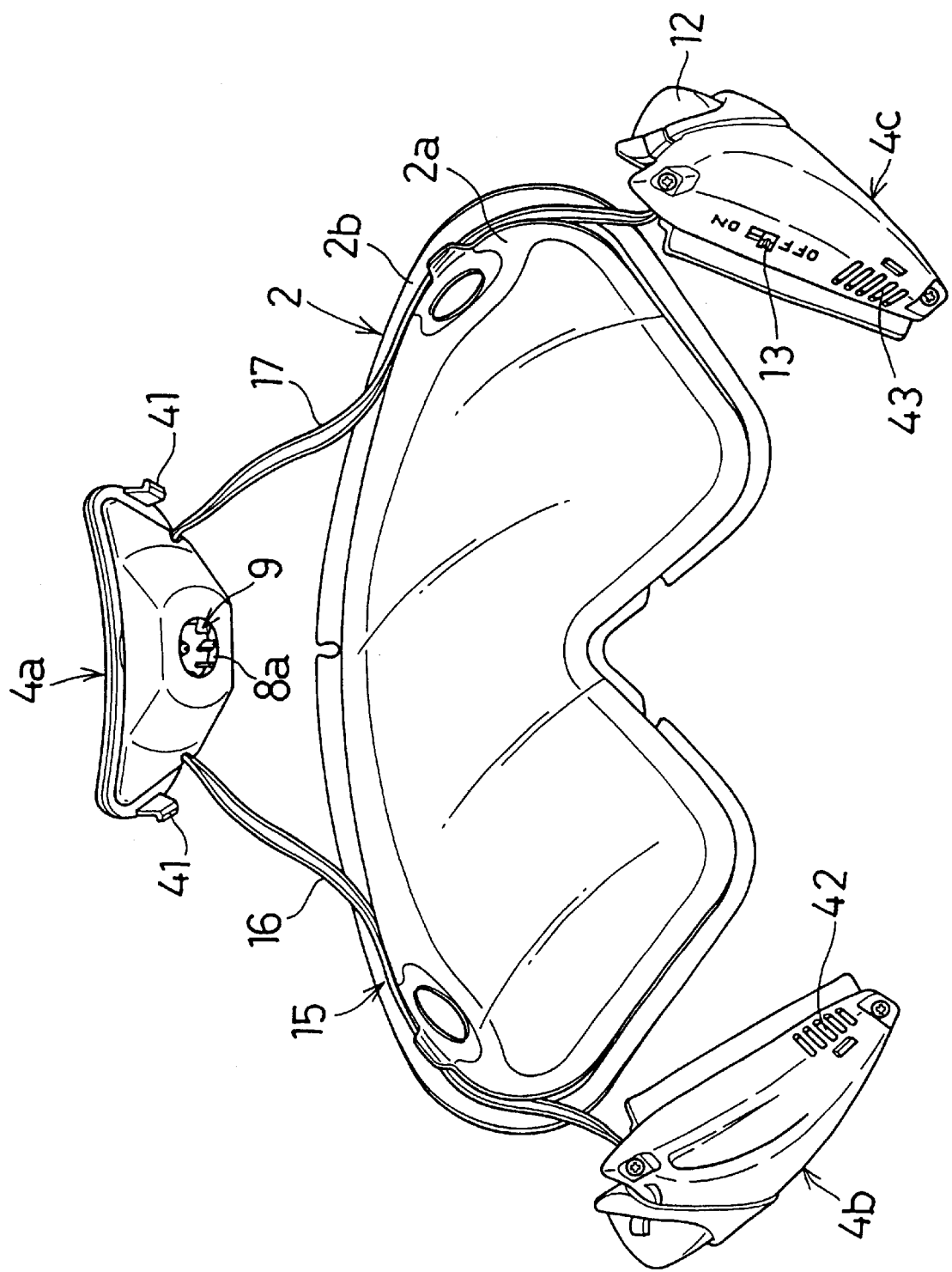
FIG. 7 is a view showing the electric wiring provided along with a step formed on the inside of an upper peripheral edge area of the goggle lens of the sports goggles of the present invention.
Figure 8:
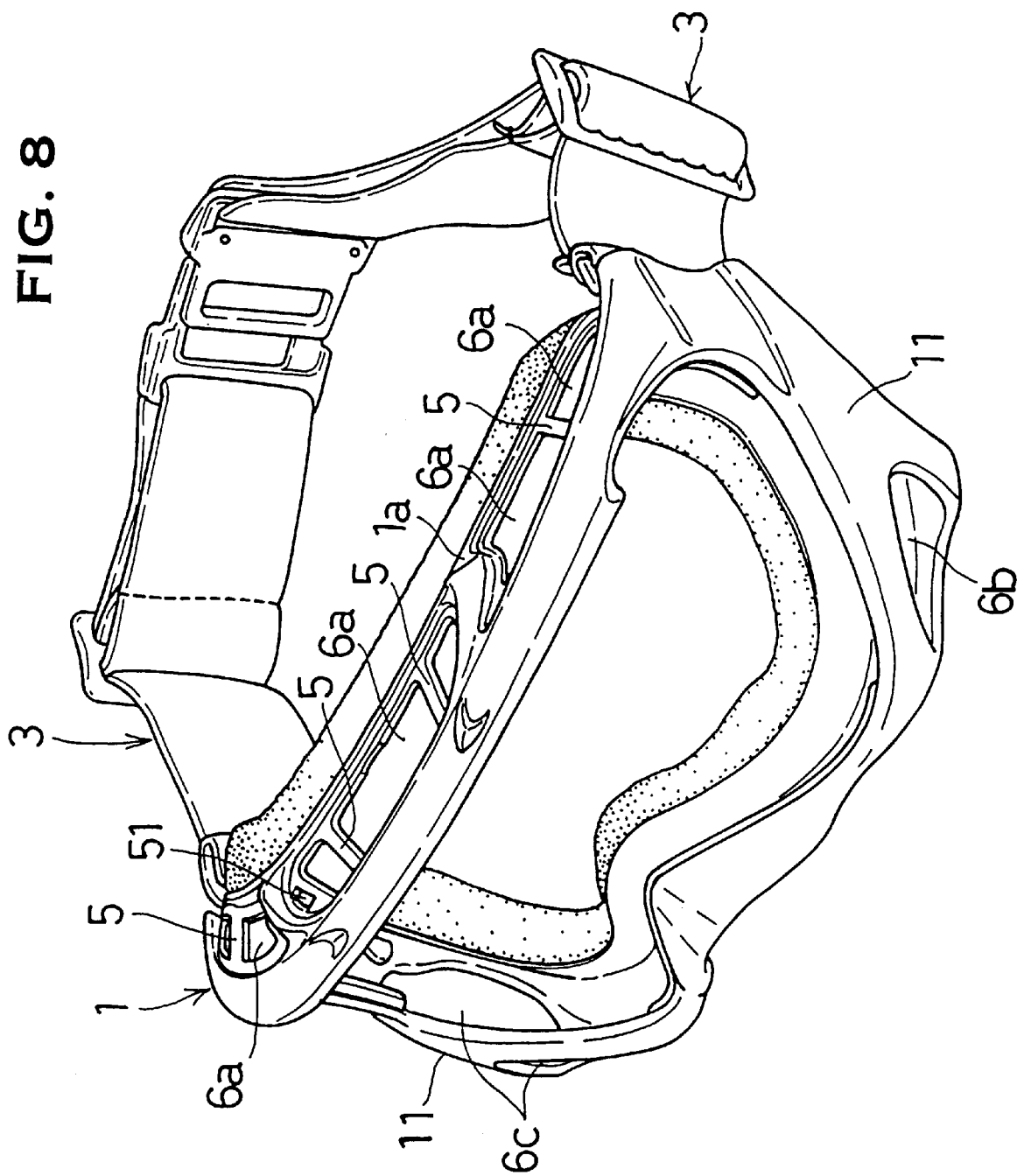
FIG. 8 is a perspective view of the sports goggles of the present invention in which all of the goggle lens, the ventilation fan system and the cover are removed.
Figure 9:
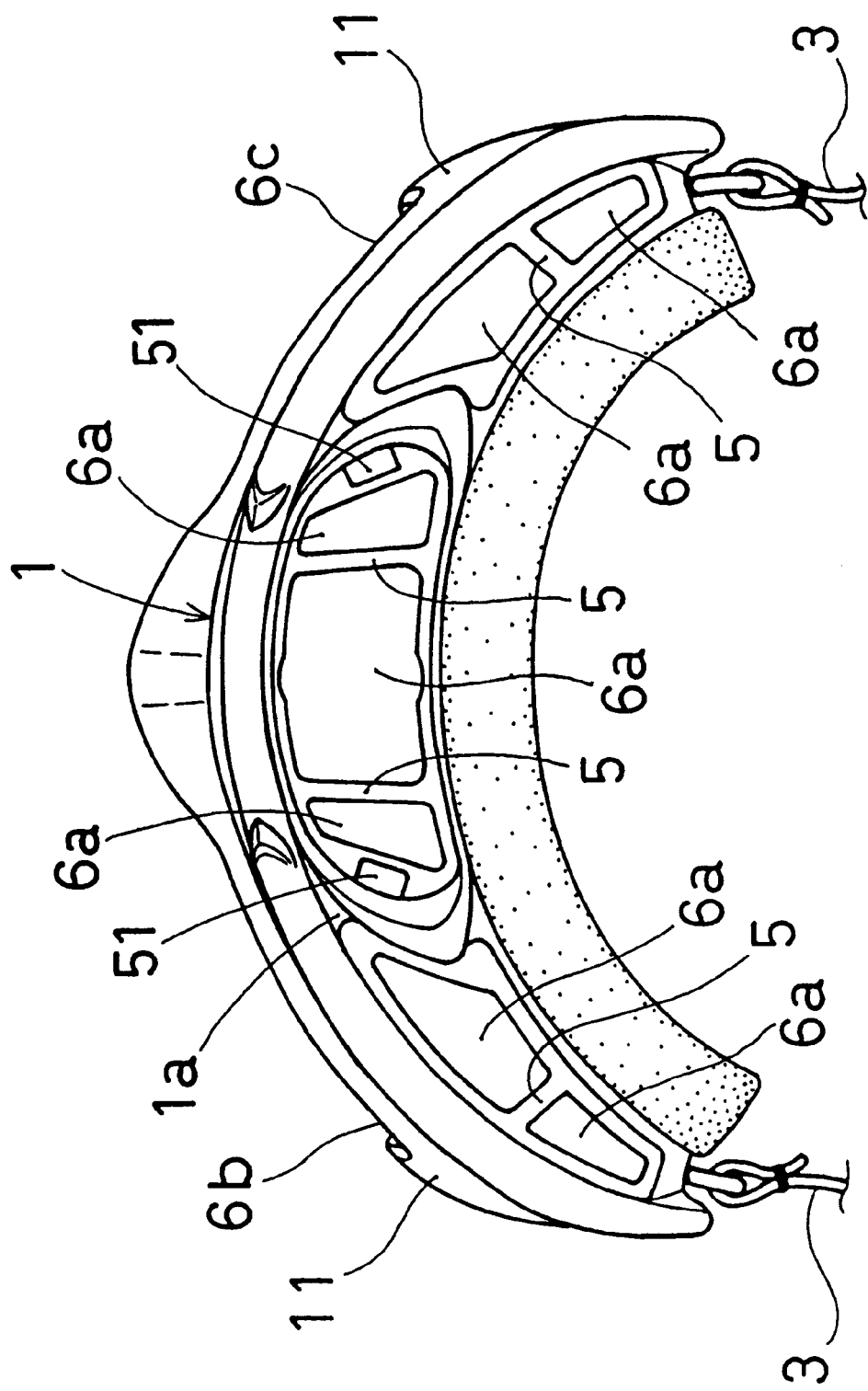
FIG. 9 is a plan view showing the sports goggles of the present invention shown in FIG. 8 in which the strap is omitted.
Figure 10:
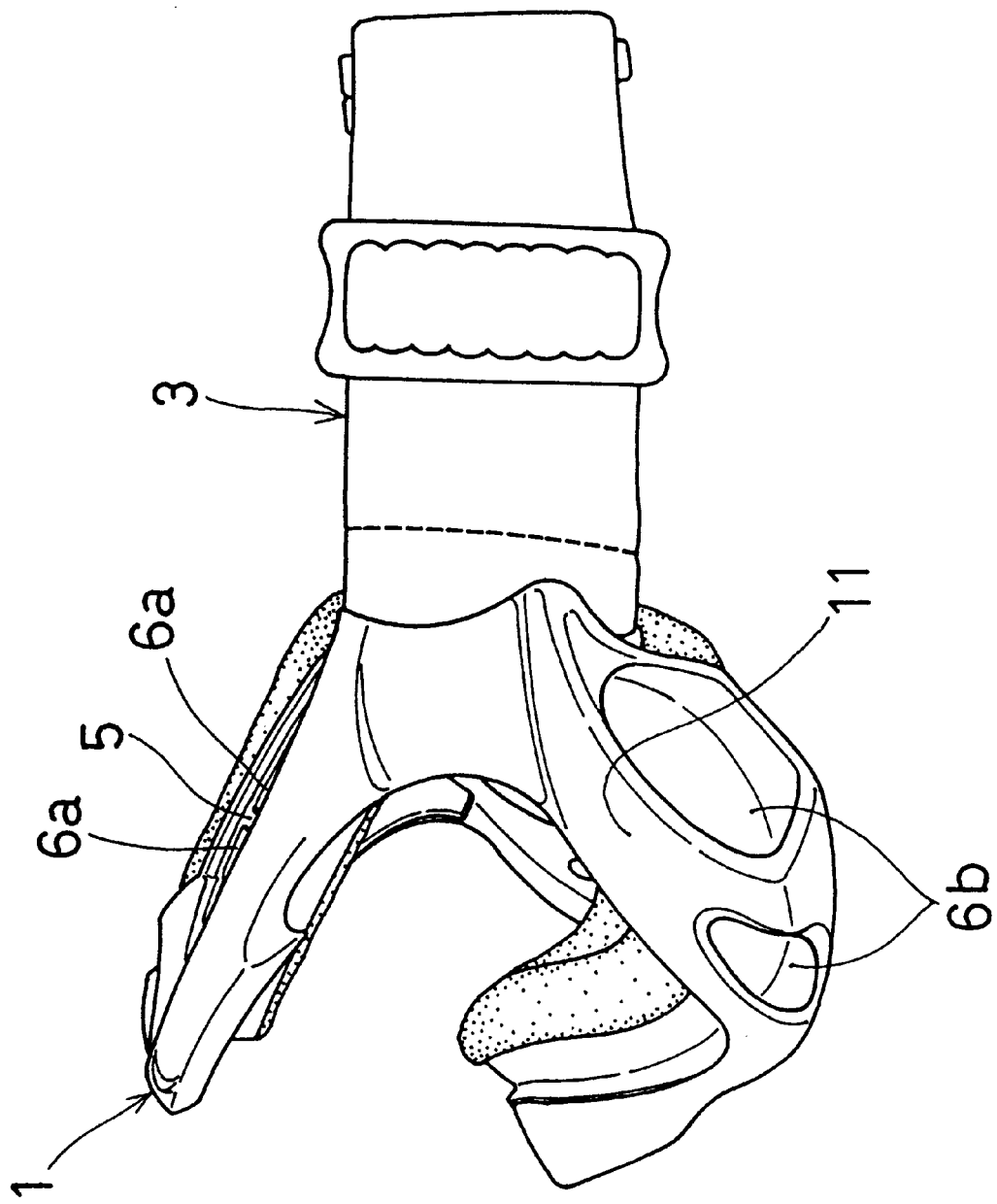
FIG. 10 is a side view of the sports goggles of the present invention shown in FIG. 8.

FIG. 7 shows more clearly the step 15 of the goggle lens 2. A wire 16 extending from the ventilation unit 4a to the power supply unit 4b and a wire 17 extending from the ventilation fan unit 4a to the switch unit 4c may be laid on the step 15, so that the wires extend along the upper peripheral edge area of the goggle lens 2, and are not exposed out of the sport goggles per se. Therefore the step 15 enables easy wiring. In FIG. 7, the wires are laid on along the entire upper portion of the step 15, but they may be placed on only along one part thereof. Furthermore, printed wiring may be employed instead of placing electric wires.

When the sports goggles of the present invention stated above are used in skiing or a motorcycle tour on a rainy day, the goggle lens or the eyeglass lens for correcting eyesight is very likely to become clouded due to high humidity. In such a case, before having the goggles on, a wearer may put the misoperation preventive switch 13 off, and, putting them on, he or she may turn the operation switch 12 on and off so as to actuate and stop the ventilation fan 9.

When the goggle lens 2 or the eyeglass lens for correcting eyesight becomes clouded as air inside of the goggles is warmed by the wearer's body temperature, the wearer turns on the operation switch 12 to actuate the ventilation fan 9. The ventilation fan 9 takes in the warmed air inside of the goggles through the inhale port 8a of the ventilation fan unit 4a and then drives it out from the exhale port 8b. And fresh cold air as much as being exhaled is inhaled through the openings 6a, 6b and 6c. Here the inside of the goggles is ventilated, and cloud on the goggle lens 2 or the eyeglass lens for correcting eyesight is cleared up. When the cloud is cleared, the operation switch 12 may be turned off to stop the ventilation fan 9. Or, in order to prevent clouding, the ventilation fan 9 may be kept on working without turning off the operation switch 12. Furthermore, right after the goggles are put on, the operation switch 12 is set to an ON state to start the ventilation fan 9 and the fan 9 may be kept functioning continuously, so that clouding of the goggle lens 2 or the eyeglass lens for correcting eyesight can be prevented.

In the sports goggles of the present invention, a wearer can easily reach the operation switch 12 by extending his or her fingers obliquely from below the sport goggles, if necessary. Namely, the wearer's hand and fingers operating the operating switch 12 will hardly get into the field of vision.

When the sports goggles of the present invention are used in a motorcycling tour and the like on a fine day, where there is less humidity and the goggle lens 2 or the eyeglass lens for correcting eyesight hardly clouds, the mode of the goggles in use may be easily modified suitable for such a case as follows.

First of all, the goggle lens 2 is removed from the goggle frame 1, and the ventilation fan unit 4a is removed from the partition frame 5 provided on the upper portion of the goggle frame 1. And the opening 6a which is now open with the partition frame 5 is covered with a permeable cover 7 made of polyurethane foam or the like. Further, the power supply unit 4b and the switch unit 4c, which are located at both lateral end areas below the right and left coupling positions of the strap 3 of the goggles, are detached from the goggle frame 1.

Figure 11:
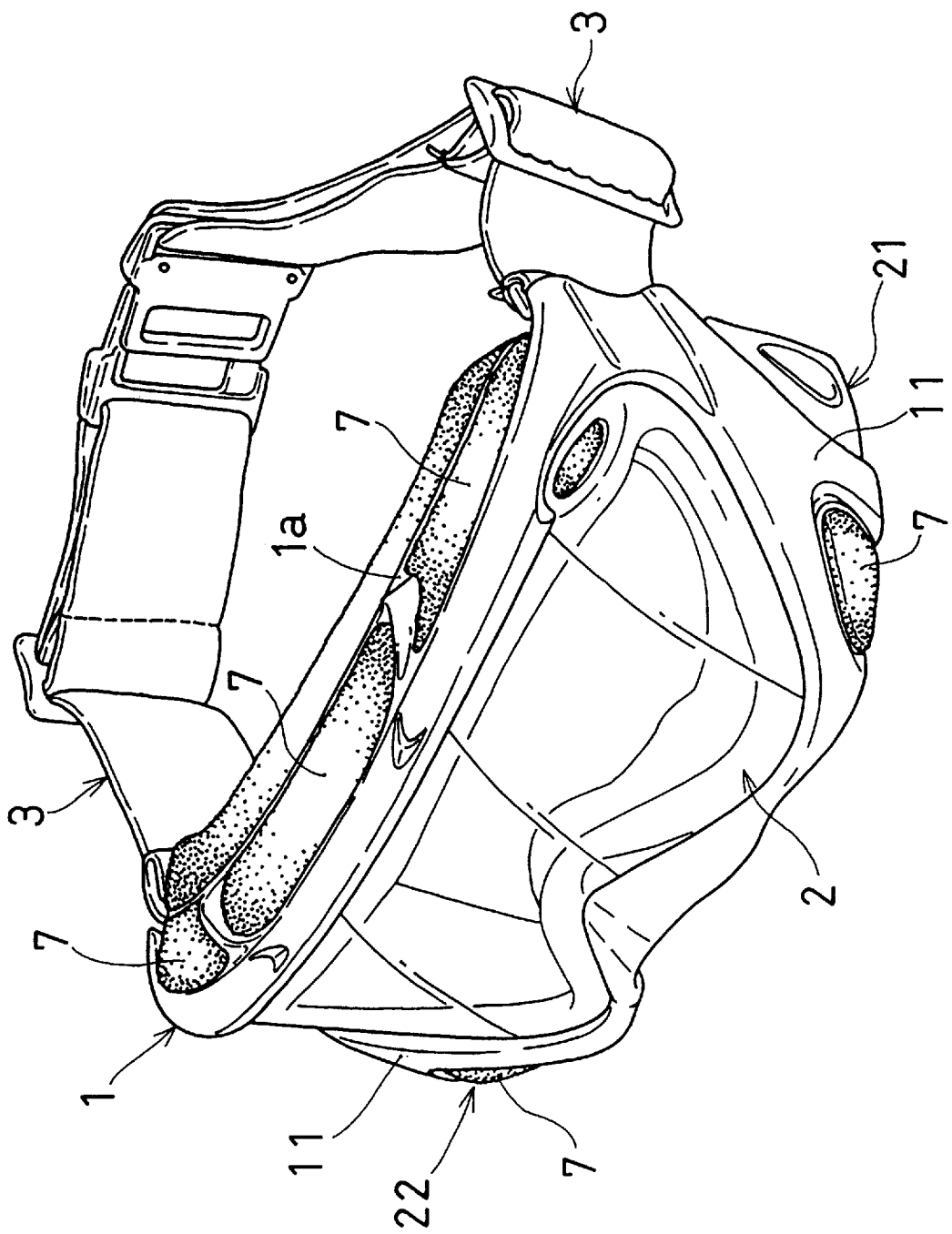
FIG. 11 is a perspective view showing a mode modified for use in case a goggle lens or an eyeglass lens for correcting the eyesight hardly become clouded.
Figure 12:
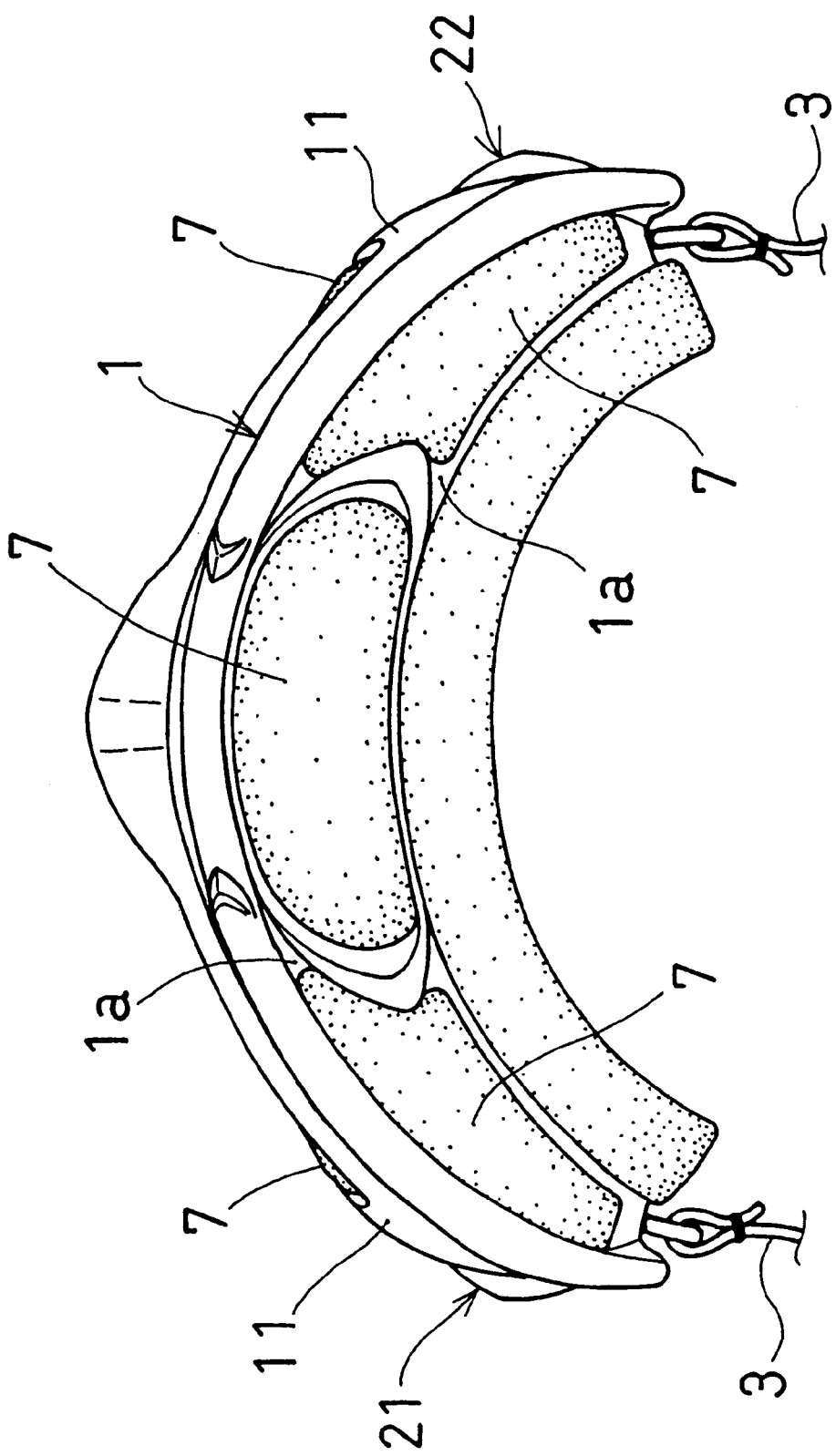
FIG. 12 is a plan view showing the sports goggles with no strap of the present invention in FIG. 11.
Figure 13:
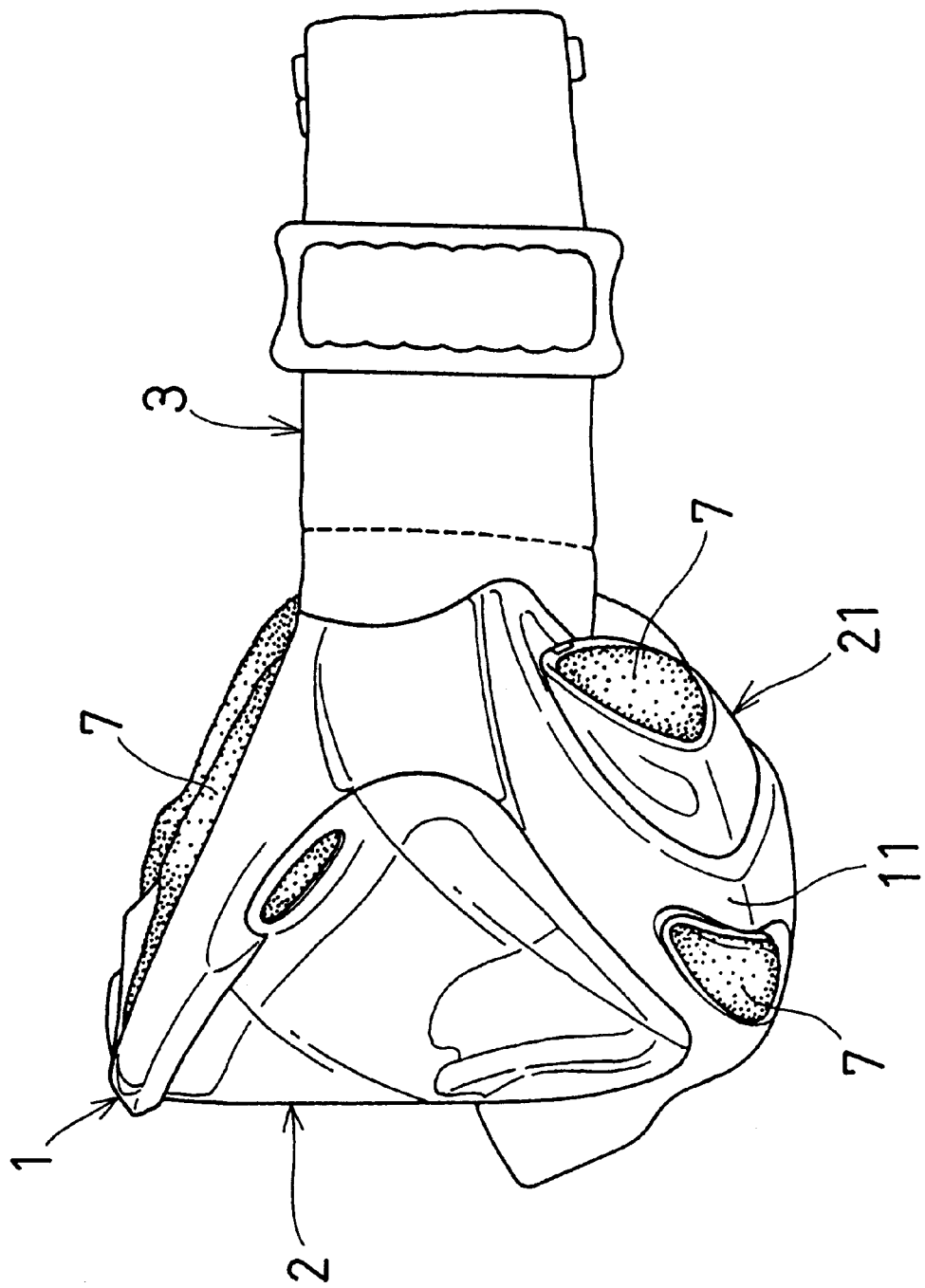
FIG. 13 is a side view of the sports goggles of the present invention shown in FIG. 11.

Empty units 21 and 22, which have the same shape as the power supply unit 4b and the switch unit 4c and have neither power source nor switch mechanism therein, are prepared, and detachably fitted in the openings 6b and 6c of the front frame 11. As a result, the sports goggles are modified into the mode shown as in FIGS. 11 to 13 and can be used in a condition where there is less humidity and the goggle lens 2 or the eyeglass lens for correcting eyesight hardly become clouded.

The empty units 21 and 22 have openings (not shown) covered with permeable covers made of polyurethane foam or the like, so that the ventilation state of the openings 6b and 6c is maintained.

Constructed as stated above, the sports goggles of the present invention not only provide comfortable fitting and high ventilation efficiency but also enable easy switching operation of the ventilation fan system, and further guarantee that a weight balance is kept well.

What is claimed is:

1. Sports goggles comprising:
   a goggle frame,
   a goggle lens fitted in the goggle frame,
   a strap coupled to the goggle frame at coupling positions on right and left sides of the goggle frame; and
   a ventilation fan system having a ventilation fan, wherein a ventilation fan unit is provided on an upper portion of the goggle frame, a power supply unit is provided on one of right and left end areas of the goggle frame below the coupling positions, and a switch unit is provided on the other of the right and left end areas.

2. Sports goggles according to claim 1 further comprising openings respectively on the upper portion of the goggle frame and on both of the right and left end areas below the coupling positions of the goggle frame and the strap, these openings respectively being kept in a ventilation state and provided with the ventilation fan unit, the supply power unit and the switch unit.

3. Sports goggles according to claim 2, wherein the ventilation fan unit, the power supply unit, and the switch unit are detachably fitted in the respective openings.

4. Sports goggles according to claim 1, wherein the switch unit has an operation switch and a misoperation preventive switch for the ventilation fan housed in the ventilation fan unit, and the operation switch is operable from outside of the goggle frame and the misoperation preventive switch is operable from inside of the goggle frame.

5. Sports goggles according claim 2, wherein the switch unit has an operation switch and a misoperation preventive switch for the ventilation fan housed in the ventilation fan unit, and the operation switch is operable from outside of the goggle frame and the misoperation preventive switch is operable from inside of the goggle frame.

6. Sports goggles according to claim 3, wherein the switch unit has an operation switch and a misoperation preventive switch for the ventilation fan housed in the ventilation fan unit, and the operation switch is operable from outside of the goggle frame and the misoperation preventive switch is operable from inside of the goggle frame.

7. Sports goggles according to claim 1, wherein a step is provided on an upper peripheral edge area of the goggle lens, and one of electric wiring and printed wiring extending from the ventilation fan unit to the power supply unit is placed on the step and one of electric wiring or printed wiring extending from the ventilation fan unit to the switch unit is placed on the step.

8. Sports goggles according to claim 2, wherein a step is provided on an upper peripheral edge area of the goggle lens, and one of electric wiring and printed wiring extending from the ventilation fan unit to the power supply unit is placed on the step and one of electric wiring or printed wiring extending from the ventilation fan unit to the switch unit is placed on the step.

9. Sports goggles according to claim 3, wherein a step is provided on an upper peripheral edge area of the goggle lens, and one of electric wiring and printed wiring extending from the ventilation fan unit to the power supply unit is placed on the step and one of electric wiring or printed wiring extending from the ventilation fan unit to the switch unit is placed on the step.

10. Sports goggles according to claim 4, wherein a step is provided on an upper peripheral edge area of the goggle lens, and one of electric wiring and printed wiring extending from the ventilation fan unit to the power supply unit is placed on the step and one of electric wiring or printed wiring extending from the ventilation fan unit to the switch unit is placed on the step.

11. Sports goggles according to claim 5, wherein a step is provided on an upper peripheral edge area of the goggle lens, and one of electric wiring and printed wiring extending from the ventilation fan unit to the power supply unit is placed on the step and one of electric wiring or printed wiring extending from the ventilation fan unit to the switch unit is placed on the step.

12. Sports goggles according to claim 6, wherein a step is provided on an upper peripheral edge area of the goggle lens, and one of electric wiring and printed wiring extending from the ventilation fan unit to the power supply unit is placed on the step and one of electric wiring or printed wiring extending from the ventilation fan unit to the switch unit is placed on the step.

* * * * *

UNITED STATES PATENT AND TRADEMARK OFFICE
CERTIFICATE OF CORRECTION

PATENT NO.   : 6,704,944 B2
DATED        : March 16, 2004
INVENTOR(S)  : Noboru Kawanishi et al.

It is certified that error appears in the above-identified patent and that said Letters Patent is hereby corrected as shown below:

<u>Title page,</u>
Item [75], Inventors, change "Noboru Kawainshi, Higashiosaka (JP); Kimio Matsumoto, Matsubara (JP); Toru Tsubooka, Sakurai (JP)" to -- Noboru Kawanishi, Higashiosaka (JP); Kimio Matsumoto, Matsubara (JP); Toru Tsubooka, Sakurai (JP) --

Signed and Sealed this

Twenty-sixth Day of July, 2005

JON W. DUDAS
*Director of the United States Patent and Trademark Office*